United States Patent
Anthony

[19]

[11] Patent Number: 5,849,008
[45] Date of Patent: Dec. 15, 1998

[54] METHOD FOR DESTRUCTION OF THE INNER EAR SPECIAL SENSORY EPITHELIUM TO RELIEVE POSITIONAL VERTIGO

[76] Inventor: Phillip F. Anthony, 901 Hemphill, Fort Worth, Tex. 76104

[21] Appl. No.: 638,702

[22] Filed: Apr. 26, 1996

[51] Int. Cl.⁶ .................................................. A61B 17/36
[52] U.S. Cl. ............................................. 606/15; 128/897
[58] Field of Search ................. 606/13–16; 128/897–98; 600/25; 623/10

[56] References Cited

U.S. PATENT DOCUMENTS

| | | |
|---|---|---|
| 4,538,609 | 9/1985 | Takenaka et al. .................. 606/16 |
| 5,662,646 | 9/1997 | Fumich .................................. 606/15 |

FOREIGN PATENT DOCUMENTS

| | | | |
|---|---|---|---|
| 0653256 | 4/1993 | Australia ................................ 606/15 |
| 1198481 | 12/1985 | Canada ................................... 606/16 |

*Primary Examiner*—John P. Lacyk
*Attorney, Agent, or Firm*—Arthur F Zobal

[57] ABSTRACT

A process is provided for destroying the calcium carbonate crystal producing utricular macula in the inner ear of a human. An aperture is formed through the footplate of the stapes bone; the probe end of a laser is inserted into the aperture; the laser is actuated to apply energy to the ultricular macula, and the probe is removed from the ear. The laser probe has a unique shape and configuration.

7 Claims, 3 Drawing Sheets

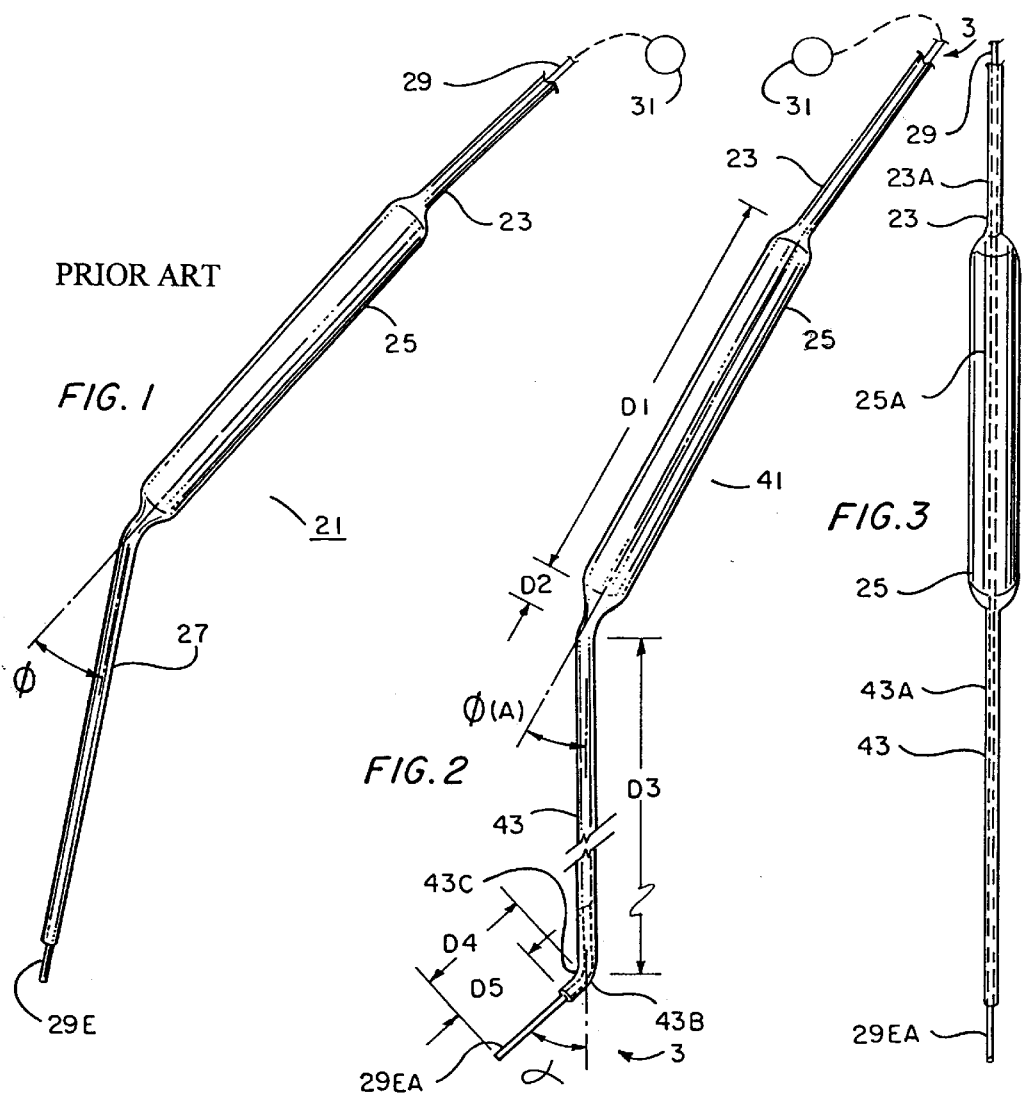

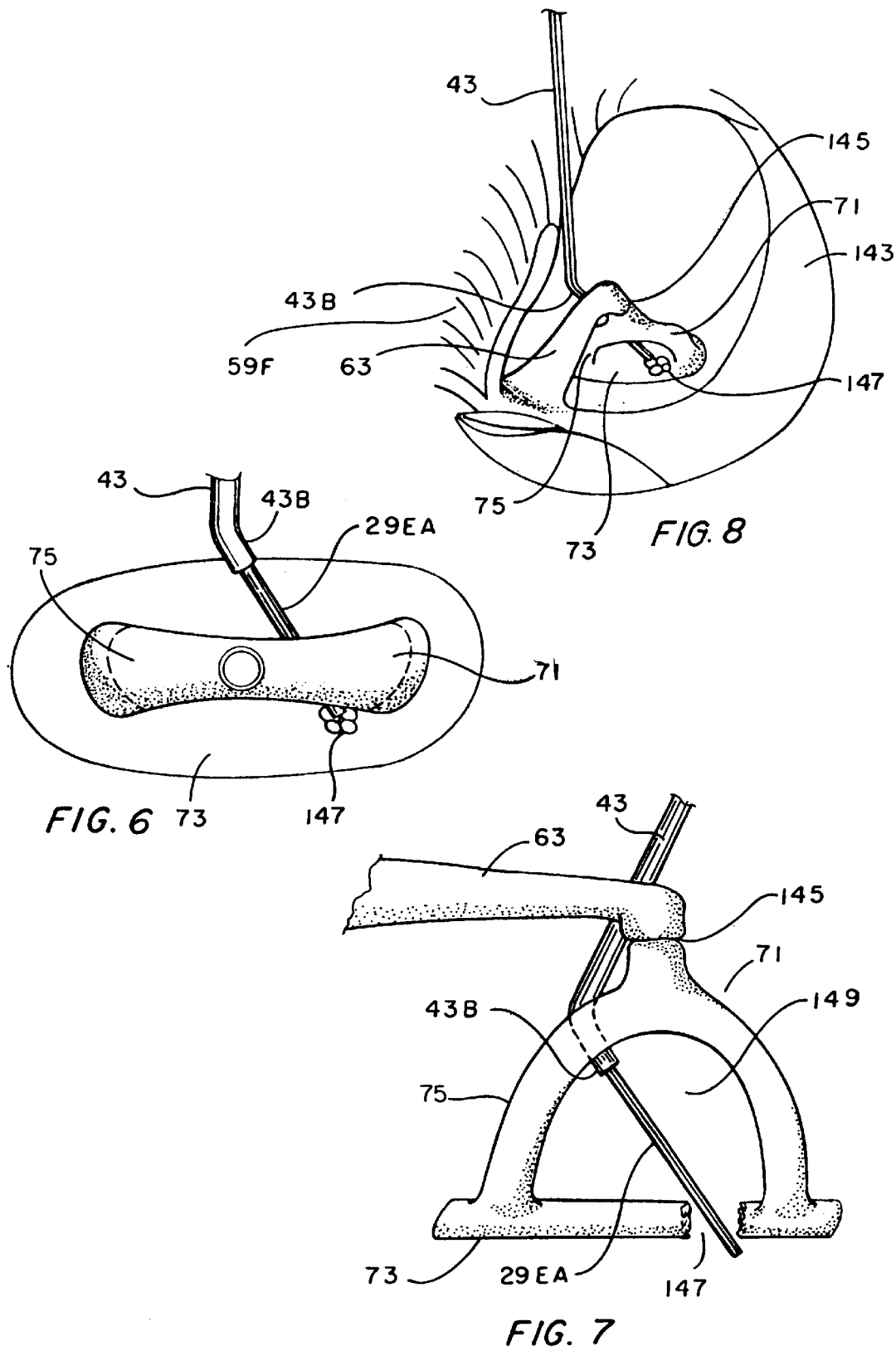

METHOD FOR DESTRUCTION OF THE INNER EAR SPECIAL SENSORY EPITHELIUM TO RELIEVE POSITIONAL VERTIGO

BACKGROUND

Approximately three million people of the 250 million people in the United States suffer from vertigo of some duration each year. Vertigo is the most common physician visit diagnosis in patients over 65 years of age. Seventeen percent of patients who have vertigo have benign paroxysmal positional vertigo. This application is directed to a new technique for the treatment of benign paroxysmal positional vertigo (positional vertigo).

PRIOR ART

NATURAL HISTORY

Positional vertigo is characterized by vertigo when the patient moves into the affected-ear-downward position. The patient may also have symptoms of vertigo with looking up, or looking down. The diagnosis is clinically confirmed by placing the patient in the affected-ear-down position and observing a characteristic rotary jerking motion of the eyes. The natural history of positional vertigo is one of spontaneous remission. Recurrence is common and can last from weeks to months. One ear is usually involved but reports of 15% of bilateral ear involvement have been made.

Positional vertigo is caused by dislodgment of naturally occurring inner ear calcium carbonate crystals 121 (FIG. 5). When these crystals fall from their normal position in the inner ear (utricular macula) 123, they hit the motion sensor of one of the inner ear rotation sensors (the posterior semicircular canal). When the patient places the affected ear downward, the loosened crystal 121L causes motion of the rotation sensor 127 causing the patient to sense vertigo. These symptoms typically resolve when the loosened crystal 121L dissolves in the surrounding endolymphatic fluid 95. When the vertigo fails to resolve (presumably because the crystal did not dissolve) or recurrence of the vertigo becomes a clinical problem, then a treatment is indicated.

Past Treatment For BPPV

Posterior semicircular canal treatments

There are three surgical treatments which cause positional vertigo to stop. The first technique involves cutting the sensory nerve 125 to the abnormally functioning rotation sensor 127. Unfortunately this technique causes a high incidence (8–40%) of injury to the inner ear hearing. The second technique is the mechanical occlusion of the posterior semi-circular canal 99. This technique requires that the semi circular canal is opened 131 and the entire canal between points 131 and 133 is occluded. This technique is effective but causes a large amount of transient postoperative vertigo. A third treatment technique uses localized laser energy heat to constrict and occlude the membranous posterior semi-circular canal. The laser-induced occlusion technique is done by thinning the bone over the semicircular canal and applying a laser burn to the thin bone at position 131. All of these techniques require a general anesthetic and cause a large amount of postoperative vertigo and can cause some hearing loss in the older patient population.

Utricular macula treatments

In the guinea pig, removing the stapes bone and applying the argon laser beam to the organ that creates calcium carbonate crystals (utricular macula) causes atrophy of the utricular macula and disappearance (presumably by dissolving) of all calcium carbonate crystals of the utricular macula, by ten weeks after the laser irradiation.

There has been one Japanese case report that is pertinent to this application. A patient with positional vertigo was treated by the laser destruction of three areas of the inner ear (1) laser cutting of the nerve to the posterior semi-circular canal sensor 125, (2) total removal of the stapes bone 71, 73, 75 with irradiation of the utricular macula 123 and (3) irradiation of the utriculo-ampullary nerve 124. The patient's vertigo stopped. This procedure included cutting the nerve to the post SCC which is a well recognized treatment for positional vertigo but has an 8–40% incidence of hearing loss. Two other procedures were done but which of the three procedures had the beneficial effect was not known.

PRIOR ART IN OTHER TECHNIQUE ASPECTS

Creating holes in the stapes footplate, primarily for removing the stapes in hearing reconstruction surgery, is a well documented procedure. Small hand held tool mechanical techniques, use of a small micro drill, the argon laser and the $CO_2$ laser for creating holes in the stapes footplate 73 are used in hearing reconstruction.

Hand held fiber optic laser conducting devices have been used and are commercially available for use in the middle ear. Straight fiber optic devices with short extension of the fiber optic outside its surrounding metal container are available as a Horn modification of an Endo-Optik device. A gently curved Gherini Endo-Optik fiber optic device is also available. The curve is approximately 30 degrees of a broad gentle radius and extension of the fiber optic tip from the metal structural tube. The device of this application is of a different length, has an angle near the hand holding portion and an angle at the working end of greater degree and much shorter turning radius than other available devices. Additionally, the device of this application has a protrusion of the fiber optic component to a much greater degree to allow placement of this component through the arch of the stapes 71, 75.

Closure of the stapes footplate opening is a well recognized procedure. Closures of natural leaks of fluid from the inner ear around the base of the stapes footplate 73 into the air containing middle ear space is recognized. Closure of a leak of inner ear fluid into the middle ear by the placement of tissue on top of the stapes footplate 73 with that tissue held under the arch of the stapes 71, 75 is a well recognized procedure. Additionally the placement of any of number of types of tissue (fat, muscle or fibrous tissue) over the opening into the inner ear created during total stapes bone 71, 73, 75 removal for hearing reconstruction is well documented.

SUMMARY OF THE INVENTION

My invention relates to a technique for the destruction of inner ear special sensory epithelium using a laser through a hole of variable size in a specific location in the footplate of the stapes bone. The method when directed to the utricular macula at certain laser intensity settings causes the resolution of positional vertigo. No other areas of treatment are necessary using this method to treat positional vertigo nor is removal of the stapes bones necessary for this treatment.

The invention includes a laser probe having a unique shape or configuration and dimensions for delivering the laser energy through the hole in the stapes footplate to the utricular macula. All existing laser fiber optic probes are designed to deliver laser energy to the middle ear 61, 63,

145, 71, 73, 75. The laser probe of the invention is designed to deliver laser energy to the inner ear 91, 99, 101, 93, 95, 121, 123, 124.

BRIEF DESCRIPTION OF THE DRAWINGS

FIG. 1 illustrates a conventional prior art laser probe used for surgery of the human ear.

FIG. 2 illustrates the laser probe of the invention.

FIG. 3 is a view of FIG. 2 taken along the lines 3—3 thereof.

FIG. 4 illustrates the outer ear, middle ear, and inner ear of a human.

FIG. 6 is a top view of the stapes bone and the laser probe of FIGS. 2 and 3.

FIG. 7 is a side view of the stapes bone and the laser probe of FIGS. 2 an 3.

FIG. 8 is another view of the stapes bone and the laser probe of FIGS. 2 and 3.

DESCRIPTION OF THE PREFERRED EMBODIMENTS

Figure 5:
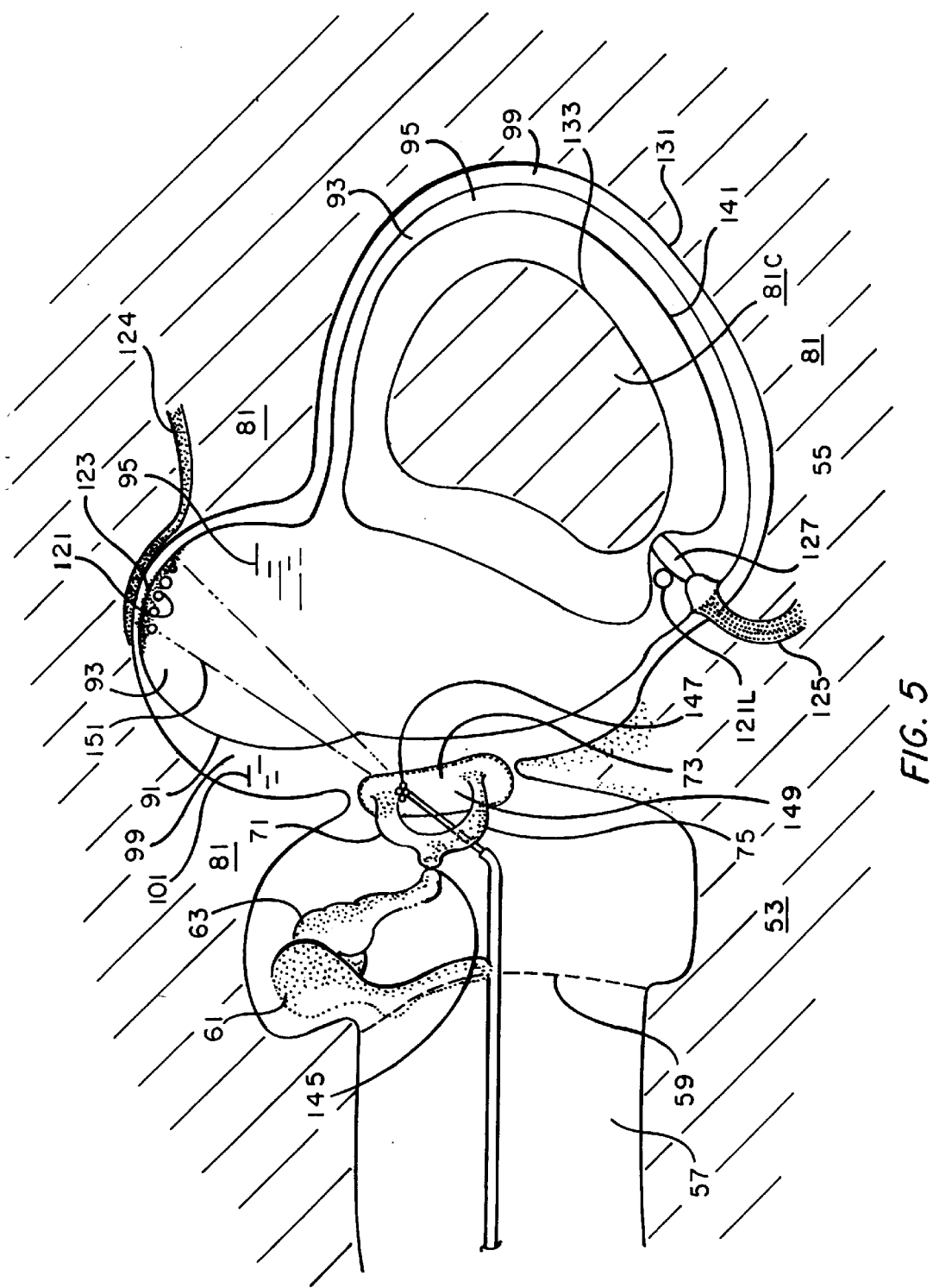
FIG. 5 is a view of the middle and inner ear of a human illustrating the use of the laser probe of FIGS. 2 and 3.

Referring to FIG. 1, a prior art laser probe that has been used for middle ear operations is shown at 21. The probe 21 as well as its fiber optic member is removably coupled to a laser source 31. The probe 21 comprises a flexible tubular cable 23 leading to a hollow handle 25 which has a metal tube 27 extending therefrom. A fiber optic member 29 extends from a laser source 31 through members 23, 25 and 27 to an end 29E which exits the tube 27. The tube 27 is straight and extends at an angle theta relative to the handle 25 of about 45 degrees. It is absolutely not possible to use the probe of FIG. 1 to carry out the process of the present invention.

The probe of the invention for carrying out the new process is shown 41 in FIGS. 2 and 3. The probe 41 as well as its fiber optic member is removably coupled to the laser source 31. The probe 41 comprises the fiber optic member 29 extending from a laser source 31 through an aperture 23A of a flexible tubular cable 23, through an aperture 25A of tubular handle 25 and through an aperture 43A of a metal tube 43. The fiber optic member 29 exits from the end of tube 43 forming a probe end 29EA. Members 23, 25 and 31 of FIGS. 2 and 3 are the same as members 23, 25 and 31 of FIG. 1. The angle theta (A) between the axis of the handle 41 and the axis of the tube 43 is greater than the angle between the axis of the handle 25 and the axis of the tube 27 of FIG. 1. In addition, the lower end of the tube 43 is bent at 43B defining an angle alpha between the axis of the probe end 29EA and the axis of the elongated portion of tube 43. The end 29EA of the probe of FIGS. 2 and 3 is greater than the end 29E of the probe of FIG. 1. The bent portion 43B of the tube 43 maintains the axis of the probe end 29EA at the angle alpha relative to the axis of the elongated portion 43 of the probe.

Referring to FIGS. 4 and 5 the outer ear, external ear canal, middle, and inner ear of a human are identified by reference numerals 51, 57, 53, and 55 respectively. Members 59, 61 and 63 are the eardrum, malleus and incus respectively. Member 71, 73, 75 are the stapes bone, and members 77 are the semicircular canal.

Referring to FIG. 5, the cross hatching 81 indicates bone. Member 91 is a transparent membrane which forms and defines a endolymphatic fluid compartment 93 containing transparent endolymphatic fluid 95. The fluid compartment 93 also extends around the center bone structure 81C.

The space 99 between the membrane 91 and the outer bone structure 81 is a fluid compartment containing transparent perilymphatic fluid 101.

In carrying out the process, the patient is sedated and the external ear canal is injected with 0.5% xylocaine with 1:25,000–200,000 epinephrine to anesthetize the ear canal and limit bleeding. A routine deep ear canal skin incision is made and the ear drum is folded forward as illustrated at 59F in FIG. 8. When the stapes bone is not easily seen, the ear-drumsupporting bone 143 (See FIG. 8) is removed with a bone curette or microdrill. An Argon laser beam is brought close to the stapes bone using a 200 micron hand-held fiber optic cable (HGM Endo-otoprobe -Horn modification). The Argon laser is set at 1.2 watts for 0.1 sec duration. Any fibrous bands in the area of the stapes bone are removed using the laser. A small piece of gelfoam with 1: 1000 adrenalin is placed around the stapes bone for 2 minutes to prevent bleeding during the procedure. The joint 145 between the incus 63 and the stapes bone 71, 73, 75 is separated using a right angle hook and a small knife. The hand held laser probe 21 with Argon laser settings of 1.2 watts and 0.1 sec per laser burn is used to create a 4 to 6 contiguous 0.5–2 mm laser burns in a rosette pattern 147 in the back top (posterior superior) portion of the stapes footplate 73 just in front of the top portion of the back arch of the stapes bone 71. A 10 second pause between each burst of laser energy allows dissipation of the heat from the laser target site. The rosette of laser burn chars is gently broken with a straight pick.

The laser energy settings are changed to 3.5 watts and 0.5 seconds duration. The new probe 41 is connected to the laser. The probe 41 is passed through the opening 149 of the arch of the stapes 71, 73, 75 and through the hole 147 in the stapes footplate 73. If the amount of area on the probe-insertion-side of the stapes superstructure 71, 75 is too small, the stapes superstructure can be rocked to one side or the other, usually allowing the probe insertion procedure to be completed. A single burst of Argon laser energy 3.5 watts and 0.5 seconds in duration is administered through the 41 probe. The laser energy beam 151 passes through the inner ear perilymphatic fluid 101, then passes through the transparent membranous labyrinth tissue 91, through the endolymphatic fluid 95, and impacts the tissue of the calcium carbonate crystal producing utricular macula 123. The probe is removed from the hole 147 in the stapes footplate 73 and from under the stapes superstructure 71, 75. The probe is then removed from the ear. A small incision is created behind the ear to take a small amount of tissue. The tissue piece is placed under the stapes arch 71, 75 to close the laser bum rosette 147 opening into the inner ear. The stapes arch 71, 75 holds the tissue in place sealing the laser created hole in the stapes footplate.

This method is unique in that it allows destruction of inner ear special sensory epithelium (in this case the calcium carbonate crystal producing utricular macula) but is extendable to other special sensory epithelium of the inner ear using laser energy delivered through a uniquely placed hole in the footplate of the stapes bone (whether that hole is created with a small handheld instrument, drill or a laser). The technique is atraumatic enough to be done under local anesthetic rather than a general anesthetic. The method causes the resolution of BPPV by the destruction of only the calcium carbonate crystal producing utricular macula (not by some unknown combination of three simultaneous procedures). The method involves the development and description here of a device for delivering Argon laser energy to the utricular macula of humans. This device is different from previous devices in its lengths, angles and the length of exposed fiber optic extending from the supporting metal tubing 43, 43B which allows the device to fit through the arch of the stapes bone 71, 75. Although the new laser probe device described is used with the Argon laser in this method description, the new laser probe configuration could be used to deliver laser energy with another non Argon laser to the utricular macula of the human.

Referring to FIGS. 2 and 3, in one embodiment, D1 is equal to 100 mm, D2 is equal to 1 mm, D3 is equal to 74 mm, D4 is equal to 4.25 mm; and D5 is equal to 4 mm. The diameter of the fiber optic member and 29EA may be 200 microns. Theta (A) is of the order of 10–45 degrees and alpha is of the order of 35–55 degrees.

I claim:

1. A method of the destruction of human inner ear special sensory epithelium, wherein the ear comprises a stapes bone with a footplate, comprising the steps of:

forming an aperture through the footplate of the stapes bone of a persons ear, inserting the end of a laser probe into the outer ear, at least within the arch opening of the stapes bone and into said aperture formed through the footplate of the stapes bone, operating said laser to apply laser energy to a selected component of the inner ear, and removing said laser from the ear.

2. The method of claim 1, wherein the ear comprises an utricular macula, comprising the step of:

applying said laser energy to the utricular macula in the inner ear for destroying the utricular macula.

3. A laser probe comprising:

a fiber optics member having a first end to be coupled to a laser source and an opposite second end for applying laser energy to an object, a tubular handle having a first end and an opposite second end, a tubular support member having a first end and a second opposite free end, said first end of said tubular support member being coupled to said second end of said tubular handle, said fiber optics member extending through said tubular handle and said tubular support member by way of said first end of said tubular handle and beyond said second opposite free end of said tubular support member, said tubular handle having a central axis, a substantial portion of said tubular support member having a central axis, in a plane passing through said probe, said central axes of said tubular handle and said tubular support member define an angle between about 10–45 degrees, in said plane, said opposite free end of said tubular support member extends from a bend position toward said central axis of said tubular handle for supporting said opposite free end of said fiber optic member at an angle relative to said central axis of said tubular support member of between about 35–55 degrees, said fiber optic member extending beyond said second opposite end of said tubular support having a cross-sectional size such that it may be inserted at least within the arch opening of the stapes bone of a human.

4. The laser probe of claim 3 wherein:

the dimension of said probe from said bend position to said opposite free end of said fiber optic is about 4.25 mm.

5. The laser probe of claim 3 wherein:

said opposite second end of said fiber optic member extends beyond said opposite free end of said tubular support member a distance of about 4 mm.

6. A method of the destruction of human inner ear special sensory epithelium, wherein the ear comprises a stapes bone with a footplate, comprising the steps of:

forming an aperture through the footplate of the stapes bone of a persons ear, obtaining a laser probe having an end with a cross-section and a shape sufficient to be inserted at least within the arch opening of the stapes bone of a persons ear, inserting said end of said laser probe into the outer ear, at least within the arch opening of the stapes bone and into said aperture formed through the footplate of the stapes bone, operating said laser to apply laser energy to a selected component of the inner ear, and removing said laser from the ear.

7. A laser probe comprising:

a fiber optics member having a first end to be coupled to a laser source and an opposite second end for applying laser energy to an object, a tubular handle having a first end and an opposite second end, a tubular support member having a first end and a second opposite free end, said first end of said tubular support member being coupled to said second end of said tubular handle, said fiber optics member extending through said tubular handle and said tubular support member by way of said first end of said tubular handle and beyond said second opposite free end of said tubular support member, said tubular handle having a central axis, a substantial portion of said tubular support member having a central axis, in a plane passing through said probe, said central axes of said tubular handle and said tubular support member define a first acute angle, in said plane, said opposite free end of said tubular support member extends from a bend position toward said central axis of said tubular handle for supporting said opposite free end of said fiber optic member at a second acute angle relative to said central axis of said tubular support member, said fiber optic member extending beyond said second opposite end of said tubular support having a cross-sectional size such that it may be inserted at least within the arch opening of the stapes bone of a human.

* * * * *